United States Patent [19]
Kishino et al.

[11] 3,933,947
[45] Jan. 20, 1976

[54] O-ETHYL-S-PROPYL-S-BENZYL-PHOS-PHORODITHIOLATES

[75] Inventors: Shigeo Kishino, Tokyo; Akio Kudamatsu; Kozo Shiokawa, both of Kanagawa, all of Japan

[73] Assignee: Bayer Aktiengesellschaft, Leverkusen, Germany

[22] Filed: Aug. 8, 1973

[21] Appl. No.: 386,674

Related U.S. Application Data

[62] Division of Ser. No. 127,415, March 23, 1971, abandoned.

[30] Foreign Application Priority Data
Mar. 25, 1970  Japan.................................. 45-24438

[52] U.S. Cl. ................ 260/949; 260/940; 260/951; 260/954; 260/963; 424/210; 424/216; 424/217; 424/218; 424/225
[51] Int. Cl.². ..................... C07F 9/165; A01N 9/36
[58] Field of Search ..................................... 260/949

[56] References Cited
UNITED STATES PATENTS

| | | | |
|---|---|---|---|
| 2,881,201 | 4/1959 | Schrader........................ | 260/949 X |
| 2,938,919 | 5/1960 | Lorenz et al...................... | 260/949 |
| 3,309,371 | 3/1967 | DuBreuil Curry et al...... | 260/949 X |

*Primary Examiner*—Anton H. Sutto
*Attorney, Agent, or Firm*—Burgess, Dinklage & Sprung

[57] ABSTRACT

O-ethyl-S-n-propyl-S-optionally substituted-benzyl-phosphoro(thiono)dithiolates of the formula

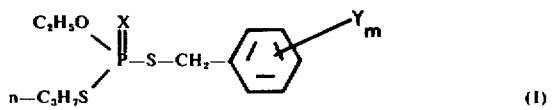

(I)

in which
  X stands for an oxygen or sulfur atom,
  Y stands for a halogen atom or a lower alkyl, lower alkoxy, lower alkylmercapto, lower alkylsulfinyl, nitro or cyano group, and
  m is 0, 1, 2 or 3, which possess insecticidal, acaricidal and nematocidal properties.

6 Claims, No Drawings

O-ETHYL-S-PROPYL-S-BENZYL-PHOSPHORODI-THIOLATES

This is a division of application Ser. No. 127,415 filed Mar. 23, 1971, now abandoned.

The present invention relates to and has for its objects the provision of particular new O-ethyl-S-n-propyl-S-optionally substituted benzyl-phosphoro(thiono) dithiolates which possess insecticidal, acaricidal and nematocidal properties, active compositions in the form of mixtures of such compounds with solid and liquid dispersible carrier vehicles, and methods for producing such compounds and for using such compounds in a new way especially for combating pests, e.g. insects, acarids and nematodes, especially insects and acarids, with other and further objects becoming apparent from a study of the within specfication and accompanying examples.

In agriculture, especially the cultivation of rice plants the damage caused by larvae of insects belonging to the Lepidoptera, such as the rice stem borer (Chilo suppressalis) and yellow rice borer (*Tryporyza incertulas*), and mites is a serious problem. Much research has been directed to the control of these harmful creatures but only several pesticides among the commercially available pesticides are effective against them; almost all of these pesticides comprise organic phosphorus compounds.

Further, since the same insecticides have been used in great amounts, there has been a tendency for harmful insects to acquire resistance to them.

The present invention provides phosphoric acid esters of the general formula

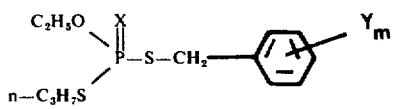

(I)

in which
X stands for an oxygen or sulfur atom,
Y stands for a halogen atom or a lower alkyl, lower alkoxy, lower alkylmercapto, lower alkylsulfinyl, nitro or cyano group, and
$m$ is 0, 1, 2 or 3.

Although Y may stand for a fluorine or iodine atom, the preferred halogens are chlorine and bromine. Preferred lower alkyl and alkoxy groups include those with an alkyl of 1 to 4 carbon atoms, namely methyl, ethyl, n- and iso-propyl, and n-, iso-, sec- and tert-butyl.

The compounds of the general formula (I) have been found to exhibit a pronounced pesticidal activity against Lepidoptera and Tetranychus, especially, against insects. As compared with active compounds of similar structure which have been described in the literature or known compounds exhibiting similar directions of activity, the novel compounds of this invention exhibit substantially improved effects and very low toxicity of warm-blooded animals.

The compounds of this invention can be used for controlling harmful insects of a broad range such as harmful sucking insects, biting insects and plant parasites. They are effective as insecticides against insects harmful to agriculture, such as insects belonging to the Coleoptera, Lepidoptera, Aphidae, Orthoptera, Isoptera and Acarina, as well as Nematodes living on plant and in the soil; accordingly, then can be used as agents for protecting plants from such pests.

The compounds of this invention exhibit an especially high insecticidal activity against insects belonging to the Lepidoptera, whose control has been difficult by conventional insecticides. Further, they exhibit a very high insecticidal activity against insects which have acquired resistance to organic phosphorus insecticides of the prior art. Still further, they are effective for controlling the rice stem borer. The compounds of the invention do not exhibit such an acute toxicity to humans as is possessed by parathion and methylparathion. Nevertheless, the insecticidal activity of the compounds of this invention is comparable or superior to that of parathion and, therefore, they can safely be used as agricultural chemicals.

The present invention provides a process for the preparation of a compound of the formula (I) in which
  a. an O-ethyl-S-n-propylhalophosphorothionothiolate of the general formula

(II)

in which Hal is a halogen atom, preferably a chlorine atom, is reacted with a benzyl mercaptan of the general formula

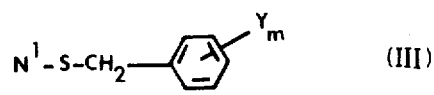

(III)

in which $M^1$ stands for a hydrogen atom or a salt-forming cation,
  or b. an O-ethyl-S-n-propyldithiophosphate of the general formula

(IV)

in which $M^2$ stands for a metal equivalent or an ammonium radical,
is reacted with a benzyl halide of the general formula

(V)

in which
Hal stands for a halogen atom,
  or c. a phosphite of the general formula

(VI)

is reacted with sulfur,
  or d. a phosphite of the general formula (VI) above is reacted with hydrogen peroxide.

The symbols X, Y and $m$ have, in the above formulae, the meanings given for formula (I).

In the synthesis of the compounds of this invention according to any of the above process variants, the reaction is preferably conducted in a solvent, which term includes a mere diluent.

An inert solvent may be used for this purpose, for example water, aliphatic and aromatic hydrocarbons which may be halogenated, such as methylene chloride, di-, tri- and tetrachloroethylenes, chloroform, carbon tetrachloride, benzine, benzene, chlorobenzene, toluene and xylene; ethers such as diethyl ether, di-n-butyl ether, dioxane and tetrahydrofuran; low-boiling aliphatic ketones and nitriles such as acetone, methylethylketone, methylisopropylketone, methylisobutylketone, acetonitrile and propionitrile; and low-boiling aliphatic alcohols such as methanol, ethanol and isopropanol.

The reaction of any process variant may be effected at temperatures within a fairly broad range, but generally the reaction is carried out at a temperature of from −20°C to the boiling point of the reaction mixture, preferably at from 10° to 100°C.

The reactants are advantageously used in substantially equimolar proportions.

M¹, in formula (III), stands preferably for a hydrogen or alkali metal, for example, sodium or potassium, atom. As benzylmercaptans which can be used in reaction variant (a), the following may be cited:

benzylmercaptan,
2-(or 4-)chloro-(or bromo-)benzylmercaptan,
2,4-(or 3,4- or 2,6-)dichloro-benzylmercaptan,
2,4,5-(or 2,3,6-)trichloro-benzylmercaptan,
2,4-(or 2,5-)dimethyl-benzylmercaptan,
4-methoxy-benzylmercaptan,
3-chloro-4-methoxy-benzylmercaptan,
4-methylthio-benzylmercaptan,
4-methylsulfinyl-benzylmercaptan,
4-nitro-benzylmercaptan,
4-cyano-benzylmercaptan, and
the sodium or potassium salts of these mercaptans.

The reaction of process variant (a) may be carried out in the presence of an acid-binder according to need (usually when M¹ is a hydrogen atom). Suitable acid-binders include hydroxides, carbonates, bicarbonates and alcoholates of alkali metals, and tertiary amines such as triethylamine, dimethylaniline and pyridine.

When the reaction is carried out in the absence of an acid-binder, the intended product of high purity can be obtained in high yield by first forming a salt, preferably a metal salt, of the appropriate benzylmercaptan, and then reacting the salt with the phosphoric acid diester monohalide.

Process variant (b) results in a compound of the formula (I) in which X is an oxygen atom. In formula (IV) M² stands preferably for an alkali metal atom, such as sodium or potassium, or an ammonium group, and in formula (V) Hal stands preferably for a chlorine or bromine atom.

As benzyl halides which may be used in the reaction of process variant (b), the following may be cited:

benzyl chloride (or bromide),
2-(or 4-)chloro(or bromo) benzyl chloride (or bromide),
2,4-(or 3,4- or 2,6-)dichlorobenzyl chloride (or bromide),
2,4,5-(or 2,3,6-)trichlorobenzyl chloride (or bromide)
2,4-(or 2,5-) dimethylbenzyl chloride (or bromide),
4-methoxybenzyl chloride (or bromide),
3-chloro-4-methoxybenzyl chloride (or bromide),
4-methylthiobenzyl chloride (or bromide),
4-methylsulfinylbenzyl chloride (or bromide),
4-nitrobenzyl chloride (or bromide), and
4-cyanobenzyl chloride (or bromide).

Process variant (c) results in compounds of the formula (I) in which X is a sulfur atom whereas process variant (d) gives rise to those in which X is an oxygen atom.

The phosphite of the general formula (VI) is conveniently prepared by the reaction between the compound of the formula

(VII)

and a benzyl mercaptan of the formula

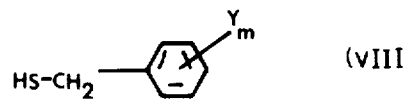

(VIII)

in the presence of an acid-binder and an inert solvent or diluent.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations, preparations or compositions, e.g. conventional pesticide formulations, preparations or compositions such as sulutions, emulsions, suspensions, emulsifiable cocentrates, wettable powders, soluble powders, oils, aerosols, pastes, fumigating powders, dusting powders, granules, pellets and tablets, etc.. These are formulated or prepared in known manner, for instance by mixing the active compounds with conventional pesticide dispersible liquid or solid diluent, carriers or extenders optionally with the use of carrier vehicle assistants, e.g. conventional pesticide surface-active agents, including emulsifying agents adhesive agent and/or dispersing agents, whereby, for example, in the case where water is used as diluent, organic solvents and/or surfactants may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, aromatic naphtha, dimethyl naphthalene, etc.), halogenated, especially chlorinated aromatic hydrocarbons (e.g. chlorobenzenes etc.), aliphatic hydrocarbons (e.g. benzine, cyclohexane, paraffins, petroleum fractions), chlorinated aliphatic hydrocarbons (e.g. methylene chloride, ethylene chloride, etc.), alcohols (e.g. methanol, ethanol, propanol, butanol, etc.), amines (e.g. ethanolamine, etc.), ethers, ether-alcohols, (e.g. glycol monomethyl ether, etc.), amides (e.g. dimethyl formamide, etc.), sulfoxides (e.g. dimethyl sulfoxide, etc.), ketones (e.g. acetone, methylethyl ketone, cyclohexanone, etc.) and/or water; as well as inert dispersible finely divided solid carriers, such as ground natural minerals (e.g. clays, talc, pyrophyllite, mica, gypsum, calcite, vermiculite, dolomite, apatite, calucium or magnesium lime, diatomaceous earth, inorganic salts i.e. calcium carbanate, pumice, etc.) and ground synthetic minerals (e.g. highly dispersed silicic acid, silicates e.g. alkali silicates, etc.); whereas the following may be chiefly considered for use as conventional carrier vehicle assistants, e.g. surface-active agents, for this purpose: emulsifying agents, such as non-ionic and/or anionic and/or cationic emulsifying agents, (e.g. polyethyleneoxide esters of fatty acids, polyethylene oxide ethers of fatty alcohols, alkyl sulfonates, aryl sulfonates, alkyl dimethyl benzyl ammonium chloride, etc., and especially alkyl arylopolyglycol ethers, magnesium stearate, sodium oleate, etc.); and/or dispersing agents, such as lignin, sulfite waste liquors, methyl cellulose etc..

Such active compounds may be employed alone or in the form of mixtures with one another and/or with such solid and/or liquid dispersible carrier vehicles, optionally with the use of carrier vehicle assistants and/or with other known compatible active agents, especially plant protection agents, such as other insecticides, acaricides, nematocides, fungicides, bactericides, herbicides, rodenticides, fertilizers or plant growth-regulating agents, etc., if desired, or in the form of particular dosage preparations for specific application made therefrom, such as solutions, emulsions, suspensions, powders, pastes, and granules which are thus ready for use.

As concerns commercially marketed formulations, these generally contemplate carrier composition mixtures in which the active compound is present in an amount substantially between about 0.1 – 95% by weight, and preferably 0.5 – 90% by weight, of the mixture, whereas carrier composition mixtures suitable for direct application or field application generally contemplate those in which the active compound is present in an amount substantially between about 0.0001 – 20%, preferably 0.001 – 5%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001 – 95%, and preferably 0.001 – 95%, by weight of the mixture.

The amount of active compound applied per unit area is usually about 150 to 10000 grams, preferably 400 to 6000 grams of active compound per hectare. However, in special cases, it may be possible to use more or less, sometimes such variations may be required.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50 – 100 microns, or even less, i.e. mist form, for example by airplane crop spraying techniques. Only up to at most about a few liters/hectare are needed, and often amounts only up to about 150 to 10000g/hectare preferably 400 to 6000g/hectare, are sufficient. In this process it is possible to use highly concentrated liquid compositions with said liquid carrier vehicles containing from about 20 to about 95% by weight of active compound or even the 100% active substance alone, e.g. about 20 – 100% by weight of the active compound.

Furthermore, the present invention contemplates methods of selectively killing, combating or controlling pests, e.g. arthropods, i.e. insects and acarids, and more particularly methods of combating at least one of insects and acarids which comprises applying to at least one of correspondingly (a) such insects, (b) such acarids, and (c) the corresponding habitat thereof, i.e. the locus to be protected, a correspondingly combative or toxic amount, i.e. an arthropodically, especially insecticidally or acaricidally, effective amount of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples.

EXAMPLE 1

24 g of potassium O-ethyl-S-n-propyldithiophosphate are dissolved in 100 ml of alcohol, and 19.5 g of 2,4-dichlorobenzyl chloride are added to the solution dropwise, followed by agitation at 70°C for 2 hours. The alcohol is removed from the reaction mixture by distillation, and the residue is dissolved in benzene, washed with water and sodium carbonate, and dried over anhydrous sulfuric acid. Benzene is removed by distillation and the residue is subjected to vacuum distillation. There are obtained 30 g of O-ethyl-S-n-propyl-S-(2,4-dichlorobenzyl) phosphorodithiolate of the formula

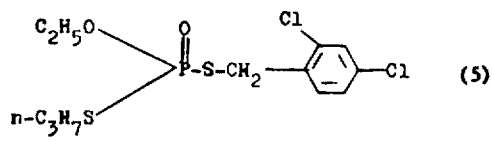 (5)

The product has a boiling point of 155°–157°C under 0.02 mm Hg and a refractive index $n_D^{20}$ of 1.5791. This compound is hereinafter designated as compound No. 5.

EXAMPLE 2

19 g of 3,4-dichlorobenzyl mercaptan are dissolved in 100 ml of benzene and 10 g of triethylamine are added to the solution. Then 19 g of O-ethyl-S-n-propyl-chlorophosphorothiolate (boiling at 70°C under 0.5 mm Hg) is added to the solution under cooling, following which agitation is continued at room temperature for a while. Then the mixture is heated at 60°–65°C to complete the reaction. The reaction mixture is washed with water, 1% hydrochloric acid and then with 1% sodium carbonate, and dried over anhydrous sodium sulfate. Distillation of the benzene gives 27 g of a colorless oil, O-ethyl-S-n-propyl-S-(3,4-dichlorobenzyl(-phosphorodithiolate of the formula

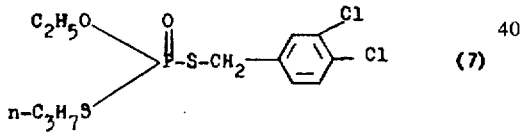

The product has a boiling point of 163°–165°C under 0.03mm Hg and a refractive index $n_D^{20}$ of 1.5796. This compound is hereinafter designated compound No. 7.

EXAMPLE 3

8 g of pyridine are added to a solution of 16 g of 4-chlorobenzyl mercaptan in 70 ml of toluene. While nitrogen gas is being introduced into the solution, 19 g of O-ethyl-S-n-propylchloro-phosphite (boiling at 48°–50°C under 1 mm Hg) are added thereto dropwise at room temperature. After completion of the addition, the mixture is agitated at 40°C for one hour, followed by the addition of 3.2 g of sulfur. Then the mixture is heated at 90°C for one hour and cooled to room temperature. The reaction liquor is diluted with 80 ml of benzene, washed with 1% hydrochloric acid and 4% sodium bicarbonate and dried over anhydrous sodium sulfate. Distillation of the solvent gives 24 g of a colorless oil, O-ethyl-S-n-propyl-S- (4-chlorobenzyl) phosphorthionodithiolate of the formula

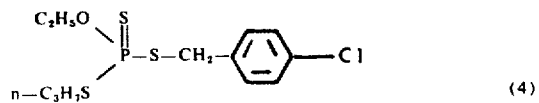

The product has a boiling point of 186°–190°C under 0.15 mm Hg and a refractive index $n_D^{20}$ of 1.6029. This compound is hereinafter designated compound No. 4.

EXAMPLE 4

The following compounds may be synthesized by methods analogous to those of Examples 1–3.

TABLE 1

$$\underset{n-C_3H_7S}{\overset{C_2H_5O}{\diagdown}}\overset{X}{\underset{\|}{P}}-S-CH_2-\!\!\!\left\langle\!\!\bigcirc\!\!\right\rangle\!\!-Y_m \qquad (I)$$

| Compound No. | X | Ym | Physical Properties Boiling Point | Refractive Index |
|---|---|---|---|---|
| 1 | S | (m=0) | 166–170°C/0.08 mmHg, | $n_D^{20}$ 1.6028 |
| 2 | O | 2—Cl | 149–151°C/0.2 mmHg, | $n_D^{20}$ 1.5707 |
| 3 | O | 4—Cl | 150–153°C/0.1 mmHg, | $n_D^{20}$ 1.5710 |
| 6 | S | 2,4—Cl₂ | | $n_D^{20}$ 1.6060 |
| 8 | S | 3,4—Cl₂ | 174–177°C/0.1 mmHg, | $n_D^{20}$ 1.6087 |
| 9 | O | 2,6—Cl₂ | 156–158°C/0.05 mmHg, | $n_D^{20}$ 1.5783 |
| 10 | O | 2,4,5—Cl₃ | 160–162°C/0.08 mmHg, | $n_D^{20}$ 1.5863 |
| 11 | S | 2,4,5—Cl₃ | | $n_D^{20}$ 1.6167 |
| 12 | O | 2,3,6—Cl₃ | 161–165°C/0.1 mmHg, | $n_D^{20}$ 1.5878 |
| 13 | S | 2,3—6—Cl₃ | | $n_D^{20}$ 1.6067 |
| 14 | O | 4—Br | 143–146°C/0.08 mmHg, | $n_D^{20}$ 1.5834 |
| 15 | O | 2,4—(CH₃)₂ | 162–167°C/0.15 mmHg, | $n_D^{20}$ 1.5589 |
| 16 | O | 2,5—(CH₃)₂ | 163–167°C/0.18 mmHg, | $n_D^{20}$ 1.5578 |
| 17 | O | 4—CH₃O | | $n_D^{20}$ 1.5544 |
| 18 | S | 4—CH₃O | | $n_D^{20}$ 1.5933 |
| 19 | O | 3—Cl,4—CH₃O | | $n_D^{20}$ 1.5720 |
| 20 | O | 4—CH₃S | | $n_D^{20}$ 1.5950 |
| 21 | S | 4—CH₃S | | $n_D^{20}$ 1.6210 |
| 22 | O | 4—CH₃S(=O)— | | $n_D^{20}$ 1.5897 |
| 23 | S | 4—CH₃S(=O)— | | $n_D^{20}$ 1.6164 |
| 24 | O | 4—NO₂ | 170–173°C/0.17 mmHg, | $n_D^{20}$ 1.5800 |
| 25 | O | 4—CN | 174–176°C/0.1 mmHg, | $n_D^{20}$ 1.5721 |

EXAMPLE 5

15 parts of compound (24), 80 parts of diatomaceous earth and clay and 5 parts of the emulsifier RUNNOX (product of Toho Kagaku Kogyo K.K., Japan) are ground and mixed together to form a wettable powder. It is diluted with water for actual application. [diatomaceous earth and clay (3:2); RUNNOX: polyoxyethylenealkylarylether]

EXAMPLE 6

30 parts of compound (5), 30 parts of xylene, 30 parts of KAWAKAZOL (product of Kawasaki Kasei Kogyo K.K., Japan), and 10 parts of the emulsifier SORPOL (product of Toho Kagaku Kogyo K.K., Japan) are mixed with stirring to form an emulsifiable concentration. It is diluted with water for actual application. [KAWAKAZOL: : aliphatic hydrocarbons with high boiling point; SORPOL: polyoxyethylenealkylarylether]

EXAMPLE 7

10 parts of compound (20), 10 parts of bentonite, 78 parts of talc and 2 parts of lignin sulfonate are formed into a mixture and it is intimately mixed with 25 parts of water. The mixture is finely divided by means of an extruding granulator to give particles of 20 – 40 mesh, followed by drying at 40°– 50°C.

EXAMPLE 8

2 parts of compound No. 3 and 98 parts of a mixture of talc and clay were ground and mixed together to form a dust. [talc and clay (3:1)]

Note: The term "parts" used in the Example (5) to (8) means weight.

EXAMPLE 9

Preparation of Test compound

Solvent: 3 parts by weight of dimethylformamide
Emulsifier: 0.1 part by weight of alkyl aryl polyglycol ether In order to prepare a suitable preparation of an active compound, one part by weight of the active compound is mixed with the above amount of the solvent containing the above amount of the emulsifier, and the mixture is diluted with water to form an aqueous preparation containing the active compound at a prescribed concentration.

Test 1: Test on tobacco cutworm (Prodenia litura) larvae:

Test procedure

Sweet-potato leaves are dipped in a preparation of the active compound prepared in Example 9, and they are dried in air and placed in a 9 cm diameter Petri dish. Then 10 of third-instar tobacco cutworm larvae are put into the dish and the dish is kept in a thermostat chamber maintained at 28°C. After 24 hours have passed, the number of the dead larvae is counted and the killing ratio is calculated.

Test 2: Test on almond moth (Ephestia cautella):

Test procedure 20 almond-moth mature larvae are put into a wire gauze vessel of 7 cm diameter and 0.9 cm height. The vessel is dipped for 10 seconds in a preparation of the active compound prepared in Example 9 at a prescribed concentration, and then the vessel is allowed to stand for 24 hours in a thermostat chamber. The number of dead larvae is counted and the killing ratio is calculated.

Test 3: Test of effects against common cabbage worm (Pieris rapae crucivora)

Test procedure

Cabbage seedling leaves are dipped in an aqueous formulation containing the active compound at a prescribed concentration, which is prepared in the same manner as in Test 1, and dried in the air. Then they are placed in a Petri dish of 9 cm diameter, and 10 common cabbage worm mature larvae are placed therein. Then the dish is kept for 24 hours in a thermostat chamber maintained at 28°C. The number of the dead larvae is counted and the killing ratio is calculated.

The results of the tests of effects against the tobacco cutworm, almond moth and green caterpillar are shown in Table 2, in which results of comparative tests using analogous compounds, identified by the letters A–L inclusive, are also shown. The entries in the Table are killing ratios expressed as percentage values.

TABLE 2

| HARMFUL INSECTS: | Tobacco Cutworm | | | Almond Moth | | | Common cabbage worm | |
|---|---|---|---|---|---|---|---|---|
| Active Compound | 1000 ppm | Concentration 300 ppm | 100 ppm | 1000 ppm | Concentration 300 ppm | 100 ppm | 1000 ppm | Concentration 100 ppm |
| 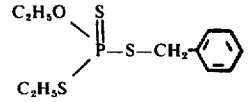 (A) | 25 | 0 | 0 | 0 | 0 | 0 | 0 | 0 |
| 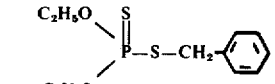 (I) | 100 | 100 | 100 | 100 | 100 | 90 | 100 | 100 |
| 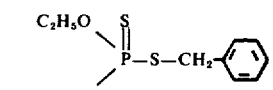 (B) | 80 | 25 | 0 | 10 | 0 | 0 | 10 | 0 |
| 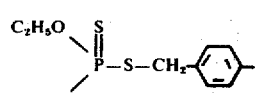 (C) | 45 | 0 | 0 | 0 | 0 | 0 | 0 | 0 |
| 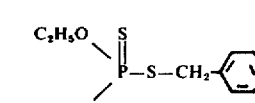 (C) | 100 | 100 | 100 | 100 | 100 | 60 | 100 | 100 |
| 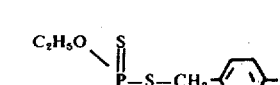 (D) | 90 | 75 | 0 | 50 | 0 | 0 | 20 | 0 |
| (E) | 15 | 0 | 0 | 0 | 0 | 0 | 0 | 0 |

TABLE 2-continued

| HARMFUL INSECTS: | Tobacco Cutworm | | | Almond Moth | | | Common cabbage worm | |
|---|---|---|---|---|---|---|---|---|
| Active Compound | Concentration | | | Concentration | | | Concentration | |
| | 1000 ppm | 300 ppm | 100 ppm | 1000 ppm | 300 ppm | 100 ppm | 1000 ppm | 100 ppm |
| (F) C₂H₅O, C₂H₅S — P(=O)—S—CH₂—C₆H₄—Cl | 60 | 0 | 0 | 30 | 0 | 0 | 5 | 0 |
| (3) C₂H₅O, n-C₃H₇S — P(=O)—S—CH₂—C₆H₄—Cl | 100 | 100 | 100 | 100 | 100 | 90 | 100 | 100 |
| (G) C₂H₅O, n-C₄H₉S — P(=O)—S—CH₂—C₆H₄—Cl | 100 | 35 | 0 | 50 | 0 | 0 | 15 | 0 |
| (H) C₂H₅O, n-C₅H₁₁S — P(=O)—S—CH₂—C₆H₄—Cl | 20 | 0 | 0 | 0 | 0 | 0 | 0 | 0 |
| (J) C₂H₅O, C₂H₅O — P(=O)—C—CH₂—C₆H₄—Cl | 0 | 0 | 0 | 0 | 0 | 0 | 0 | 0 |
| (K) C₂H₅O, C₂H₅S — P(=O)—S—CH₂—C₆H₃(Cl)—Cl | 30 | 0 | 0 | 0 | 0 | 0 | 0 | 0 |
| (5) C₂H₅O, n-C₃H₇S — P(=O)—S—CH₂—C₆H₃(Cl)—Cl | 100 | 100 | 95 | 100 | 100 | 60 | 100 | 90 |
| (L) C₂H₅O, n-C₄H₉S — P(=O)—S—CH₂—C₆H₃(Cl)—Cl | 90 | 25 | 0 | 20 | 0 | 0 | 30 | 0 |

From the results shown in Table 2 it can be seen that the phosphoric acid esters of the general formula (I) exhibit particularly excellent effects against harmful insects belonging to the Lepidoptera as compared with analogous compounds.

EXAMPLE 10

Test of effects against tobacco cutworm:

Test procedure

The test is conducted in the same manner as in Test 1 of Example 9. The results are shown in Table 3.

TABLE 3

Results of Tests of Effects Against the Tobacco Cutworm Killing Ratio(%)

| Compound No. | 300 ppm | 100 ppm |
|---|---|---|
| 1 | 100 | 100 |
| 2 | 100 | 80 |
| 3 | 100 | 90 |

TABLE 3-continued

Results of Tests of Effects Against the Tobacco Cutworm Killing Ratio(%)

| Compound No. | 300 ppm | 100 ppm |
|---|---|---|
| 4 | 100 | 95 |
| 5 | 100 | 95 |
| 6 | 100 | 80 |
| 7 | 100 | 87 |
| 8 | 100 | 70 |
| 9 | 100 | 90 |
| 10 | 100 | 65 |
| 11 | 100 | 90 |
| 12 | 100 | 90 |
| 13 | 100 | 85 |
| 14 | 100 | 87 |
| 15 | 100 | 50 |
| 16 | 100 | 60 |
| 17 | 100 | 65 |
| 18 | 100 | 60 |
| 19 | 100 | 65 |
| 20 | 100 | 85 |
| 21 | 100 | 65 |
| 22 | 100 | 85 |
| 23 | 100 | 55 |

TABLE 3-continued

Results of Tests of Effects Against the Tobacco Cutworm

| Compound No. | Killing Ratio(%) | |
|---|---|---|
| | 300 ppm | 100 ppm |
| 24 | 100 | 93 |
| 25 | 100 | 95 |
| Papthion[1] (comparison) | 80 | 35 |
| Sumithion[2] (comparison) | 60 | 20 |

Papthion[1] dimethyldithiophosphorylphenyl-acetic acid ethyl ester
Smithion[2] dimethyl (3-methyl-4-nitrophenyl) thiophosphate The compound numbers in the Table correspond to those in Example 1, 2 and 3 and Table 1

EXAMPLE 11

Test on carmine mites imagines (Tetranychus telarius):
Test Procedure

A haricot plant having two developing leaves planted in a 6 cm diameter pot is placed with 50–100 carmine mite imagines and nymphs. Two days after the infection, emulsions containing the active compound at a prescribed concentration, which is prepared in the same manner as in Example 9, is sprayed in an amount of 40 ml per pot. The pot is kept in a greenhouse for 10 days, and the control effect is evaluated. The evaluation is expressed by an index on the following scale:

Index:

3: No living imago or nymph.
2: less than 5% of living imagines and nymphs based on the untreated control
1: 5 – 50% of living imagines and nymphs based on the untreated control
0: more than 50% of living imagines and nymphs based on the untreated control.

The results are shown in Table 4.

TABLE 4

Results of Tests of Effects Against Carmine Mites

| Compound No. | Control effect index | |
|---|---|---|
| | 300 ppm | 100 ppm |
| 1 | 3 | 2 |
| 3 | 3 | 3 |
| 5 | 3 | 3 |
| 7 | 3 | 2 |
| 8 | 3 | 3 |
| 12 | 3 | 3 |
| 14 | 3 | 1 |
| 19 | 3 | 2 |
| 20 | 3 | 3 |
| 24 | 3 | 1 |
| Phenkapton[1] (comparison) | 3 | 1 |
| CPCBS[2] (comparison) | 2 | 0 |

Phenkapton[1] O,O-diethyl-S-(2,5-dichlorophenylmercapto-methyl) dithiophosphate
CPCBS[2] p-chlorophenyl-p'-chlorobenzenesulfonate The compound numbers in the Table correspond to those in Example 1, 2 and 3 and Table 1

EXAMPLE 12

Preparation of test compound 2 parts by weight of an active compound is mixed with 98 parts by weight of talc, and the mixture is ground to form a dust.

Test on root knot nematode disease (Meloidogyne hapla):
Test Procedure

The so-prepared dust is mixed with soil tainted with sweet-potato root knot nematodes in an amount such that a prescribed concentration of the active compound is attained in the soil. The treated soil is uniformly stirred and mixed, and then it is packed into pots each having an area of 1/5000 are. About 20 tomato seeds (Kurihara variety) are sowed per pot and cultivated for 4 weeks in a greenhouse. Each root is then drawn out from the soil without harming it. The damage degree is evaluated as the average of 10 roots for each group, based on the following scale.

Damage Degree

0 ... no knot (perfect control)
1 ... knots are formed slightly
2 ... knots are formed appreciably
3 ... knots are formed considerably
4 ... formation of knots is extreme (same as in untreated control).

The knot index is determined by the following equation:

$$\text{Knot Index} = \frac{\Sigma \text{ (rank value)} \times \text{(rank population)}}{\text{(whole population examined)} \times 4} \times 100$$

The results are shown in Table 5.

TABLE 5

Results of Tests of Effects Against Root Knot Nematodes

| Compound No. | Root Knot Index (%) | |
|---|---|---|
| | 100 ppm | 10 ppm |
| 3 | 0 | 1.6 |
| 5 | 0 | 5.8 |
| 14 | 0 | 3.2 |
| 20 | 0 | 0.5 |
| 24 | 0 | 8.8 |
| VC[1] (comparison) | 0 | 15.1 |

VC[1] O,O-diethyl-O-dichlorophenyl-thionophosphate

The compound numbers in the Table correspond to those in Example 1, 2 and 3 and Table 1.

It will be appreciated that the instant specification and examples are set forth by way of illustration and not limitation, and that various modifications and changes may be made without departing from the spirit and scope of the present invention.

What is claimed is:

1. Phosphoric acid esters of the general formula

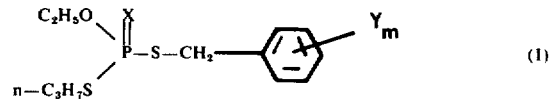

(1)

in which
X stands for an oxygen or sulfur atom,
Y stands for lower alkyl mercapto or lower alkylsulfinyl group, and
$m$ is 0, 1, 2 or 3.

2. Compounds according to claim 1 in which $m$ is 1, 2 or 3 and each Y stands for $C_1$–$C_4$ alkylmercapto or $C_1$–$C_4$ alkylsulfinyl.

3. Compound according to claim 1 wherein such compound is O-ethyl-S-n-propyl-S-(4-methylmercaptobenzyl) phosphorodithiolate of the formula

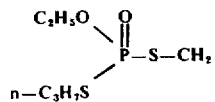
(20)

4. Compound according to claim 1 wherein such compound is O-ethyl-S-n-propyl-S-(4-methylmercaptobenzyl) phosphorothionodithiolate of the formula

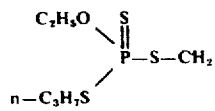
(21)

5. Compound according to claim 1 wherein such compound is O-ethyl-S-n-propyl-S-4-methylsulfinyl-benzyl)phosphorodithiolate of the formula

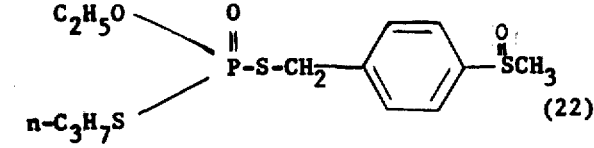
(22)

6. Compound according to claim 1 wherein such compound is O-ethyl-S-n-propyl-S-4-methylsulfinyl-benzyl)phosphorothionodithiolate of the formula

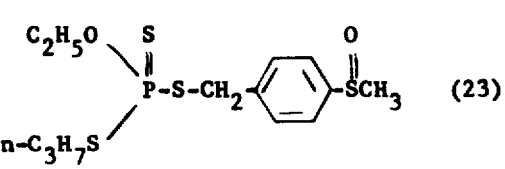
(23)

* * * * *

UNITED STATES PATENT AND TRADEMARK OFFICE
CERTIFICATE OF CORRECTION

PATENT NO. : 3,933,947
DATED : January 20, 1976
INVENTOR(S) : Shigeo Kishino et al It is certified that error appears in the above—identified patent and that said Letters Patent are hereby corrected as shown below:

Column 9, Table 2, the fifth compound thereof should be numbered -- (4) --.

Column 11, Table 2-continued, compound H, "n-$C_3H_{11}$S" should read -- n-$C_5H_{11}$S --.

Column 15, compounds 20 and 21, after "P-S-$CH_2$" insert

-- 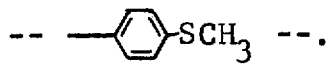 --.

Signed and Sealed this

Fourteenth Day of September 1976

[SEAL]

Attest:

RUTH C. MASON
*Attesting Officer*

C. MARSHALL DANN
*Commissioner of Patents and Trademarks*